United States Patent [19]

Sundelin

[11] Patent Number: 4,567,173

[45] Date of Patent: Jan. 28, 1986

[54] PYRIDINE, 2,2'-(2-IMIDAZOLIDINYLIDENE)DI-, COPPER IRON AND NICKEL COMPLEXES AND USE IN ANIMALS

[75] Inventor: Kurt G. R. Sundelin, Modesto, Calif.

[73] Assignee: International Minerals & Chemical Corp., Terre Haute, Ind.

[21] Appl. No.: 364,555

[22] Filed: Apr. 1, 1982

[51] Int. Cl.$^4$ .................... C07F 15/02; C07F 15/04; C07F 1/08; A61K 31/555
[52] U.S. Cl. ........................................ 514/188; 546/2; 546/256; 514/333
[58] Field of Search .................... 546/2, 256; 424/245; 514/188, 333

[56] References Cited

U.S. PATENT DOCUMENTS 3,252,802  5/1966  Cunningham ........................... 99/2

OTHER PUBLICATIONS

Kauffman et al., Chem. Abs 74, 53877a (1970).
Weiss et al., J. Amer. Chem Soc 74, 5193–5 (1952).
Hill et al., J. Organic Chem 40, 2562–5 (1975).

*Primary Examiner*—Mark L. Berch
*Attorney, Agent, or Firm*—Thomas L. Farquer; Howard E. Post

[57] ABSTRACT

Certain novel bipyridine substituted compounds, their metal complexes (Cu, Fe and Ni) which are effective to improve feed efficiency and promote growth in food-producing animals, particularly ruminants. The compounds are described by the general formula

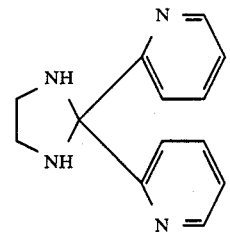

including the cupric, nickelous and ferrous salts thereof.

7 Claims, No Drawings

PYRIDINE, 2,2'-(2-IMIDAZOLIDINYLIDENE)DI-, COPPER IRON AND NICKEL COMPLEXES AND USE IN ANIMALS

BACKGROUND

There is an ever-increasing need for efficiency in producing animal protein for human consumption. As world population continues to increase, available animal feed materials increase in price, and it becomes most important that maximum growth potential from available feed materials be realized.

In monogastric food-producing animals such as swine and poultry, feed additives may be employed to protect against subclinical gastrointestinal infections, and thereby enable the target animal to realize its greatest food-producing potential. When such animals receive such feed additives on a daily basis at low levels, greater control of parasitic infections, such as coccidiosis, can be realized, and more of the feed goes to growth.

In ruminant animals such as cattle, goats and sheep, significant improvements in feed efficiency and growth can be obtained by chemical modification of the metabolism of rumen microorganisms. This may be accomplished by reducing the proportion of methane formed, and increasing the proportion of propionate at the expense of methane and acetate. Methane tends to be formed during fermentation of food in the ruminant. This represents a loss in feed energy intake, because the methane gas is lost by eructation.

Propionic acid is a much more efficient precursor of glucose, from which the animal derives its energy and growth, than acetic acid. It is, therefore, most desirable to shift the balance of rumen metabolism toward propionate production to obtain more efficient feed utilization and to promote growth in ruminants.

SUMMARY

The subject invention is directed to certain novel bipyridine substituted imidazolidinylidene compounds, their copper complexes, and their use to improve feed efficiency and promote growth in food-producing animals, particularly in ruminants. These imidazolidinylidene compounds are described by the general formula:

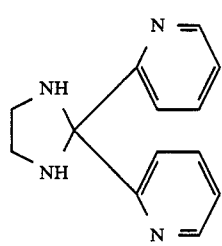

(I)

Also included in the useful compounds are the cuprous, fercupric and nickelous salts of the compounds of Formula I. The pyridine groups are both connected to the imidazolidinylidene ring at the number two carbon thereof. A particularly preferred compound of the above general formula is:

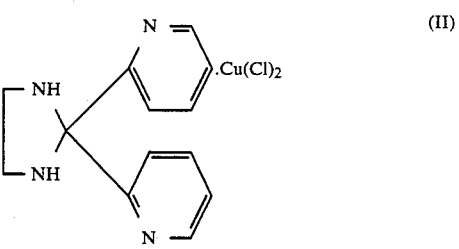

(II)

which may be described as Pyridine, 2,2'-(2-imidazolidinylidene)di-, compound with CuCl₂ (1/1). The above compound is a light green solid, and has a melting point of 155°–158° C. The calculated analysis is: C-43.2%; H-3.9%; N-15.5%; Cl-19.6%; Cu-(Balance). The above copper compound is particularly useful for growth promotion in ruminants. The compound may be administered orally in the form of physiologically acceptable salt, the above copper chloride salt being preferred. The compound is preferably administered as a feed additive, but it may take the form of a bolus which is capable of controlled release in the rumen over a predetermined period of time. Other oral administration methods include, e.g. as a drench, intubation, as a liquid supplement in solutions, suspensions, dispersions or emulsions. It is possible also to administer the composition parenterally as by injection, or by subcutaneous implant combined in implant pellet form with a suitable excipient, such as lactose, polylactides, collagen, starch, magnesium stearate, vegetable gum, cellulose acetate, dimethylpolysiloxane, ethylene vinyl acetate, or other inert, biocompatible material.

DESCRIPTION OF PREFERRED EMBODIMENTS

EXAMPLE 1

The base composition was made as set forth below:

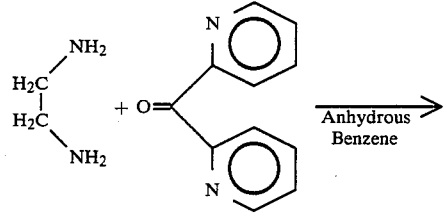

(I)

Ethylenediamine is reacted with 2,2'-dipyridylketone dissolved in dry benzene to produce pyridine, 2,2'-(2-imidazolidinylidene)di-, a yellow solid having a melting point of 107°–111° C. In the reaction procedure, about 55 parts of 2,2'-dipyridylketone (obtained from Aldrich Chemical Company, Milwaukee, Wisc.) was dissolved in about 250 parts of dry benzene. About 19 parts of ethylenediamine was added to the mixture, and it was refluxed for 16 hours, with a suitable means to remove water as it was formed. The benzene solvent was then evaporated, and the yellow solid residue was recrystallized from acetonitrile, and the product was dried under reduced pressure at 40° C.

The above compound was then reacted with anhydrous cupric chloride ($CuCl_2$) dissolved in hot, absolute alcohol as follows:

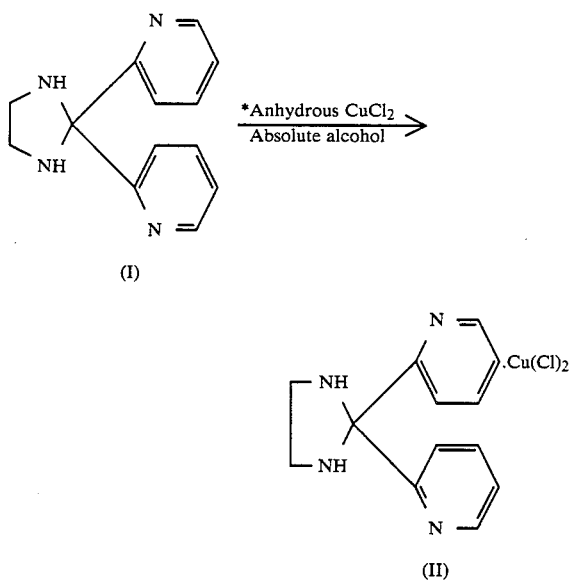

About 1.3 parts of anhydrous cupric chloride was added to a stirred solution of about 2.3 parts of the Formula I compound dissolved in about 40 parts of absolute ethyl alcohol. The mixture was stored for about 24 hours, and was then filtered. The resulting light green solid was washed with water to produce the Formula II copper complex of Formula I having a melting point of 155°–158° C., and a molecular weight of about 360.72.

EXAMPLE 2

The above Formula II composition was tested to determine its effectiveness as a feed additive for ruminants. The initial tests were in rumen fluid batch culture systems to determine the effect of the compound on volatile fatty acid/methane ratios ($VFA/CH_4$). The subject compound was used at a concentration of 75 ppm, and the effects compared to a positive control, monensin, at 12.5 ppm. A summary of the VFA, gas ($CH_4 + H_2$) production, and protein and amino acid accumulation are presented in Table 1.

Test Procedure

A 50/50 mixture of ground corn and ground alfalfa was used as the substrate for the subject rumen fluid batch culture test. The compound (Formula II) was present in the rumen fluid at 75 ppm.

On day 1, rumen fluid was obtained from mature fistulated steers on 50/50 concentrate/roughage diets. The rumen fluid (RF) was strained through three layers of gauze cloth and equilibrated with $CO_2$ gas. Wheaton serum vials (125 ml) were prepared ahead with 20 ml continuous batch buffer and 100 mg 50/50 ground corn/ground alfalfa. Controls and compounds (dissolved in acetone) were set up according to indicated levels. The vials were kept under $CO_2$ gas until 20 ml of the strained RF was added. The vials were sealed and incubated at 39° C. for 24 hours in a hot water bath. On successive days, gas samples (0.1 ml) were drawn for gas chromatography analysis before transferring 20 ml of the batch culture to another vial containing 20 ml of buffer, 100 mg substrate, and the corresponding compound. The remaining 20 ml was inoculated with 2 ml 6N HCl and centrifuged at 15,000 rpm for 15 minutes. Ether extracts were prepared for volatile fatty acid (VFA) analysis. Some minor adjustments were made in the temperatures on the Hewlett-Packard 5750 Gas-Liquid Chromatograph used for VFA analysis when the glass column used was changed from ½ inch diameter to ⅛ inch diameter.

Injection Port = 220° C.
Column Oven = 170° C.
Flame Detector = 250° C.

About 4 minutes was needed to record the sample. Results: Table 1 lists a summary of the VFA and gas data which is given in percent change from the controls.

TABLE 1

| | | Batch Rumen VFA Production Screen | | | |
|---|---|---|---|---|---|
| | | | Conc: Mu Moles/ml | | |
| Compound | - ppm | Acetate | Propionic | Butyrate | Total |
| Control | 0 | 7.5 | 15.2 | 10.0 | 32.7 |
| | | 11.0 | 19.6 | 13.3 | 44.0 |
| | | 8.1 | 17.0 | 10.5 | 35.6 |
| | | 8.2 | 15.1 | 10.7 | 34.0 |
| Mean | | 8.7 | 16.7 | 11.2 | 36.6 |
| Std. Dev. | | 1.6 | 2.1 | 1.5 | 5.1 |
| Formula II | 75 | 6.8 | 14.6 | 8.9 | 38.4 |
| Compound | | 9.2 | 15.0 | 10.2 | 34.4 |
| Mean | | 8.0 | 14.8 | 9.6 | 32.4 |
| Std. Dev. | | 1.7 | 0.3 | 1.0 | 2.9 |
| Monensin | 12.5 | 7.2 | 20.7 | 7.8 | 35.5 |
| | | 5.6 | 18.7 | 7.9 | 32.2 |
| Mean | | 6.4 | 19.7 | 7.6 | 38.8 |
| Std. Dev. | | 1.1 | 1.4 | 0.4 | 2.2 |

In the above tests, four control groups were run and the mean established. For the positive control (monensin) and the test compound (Formula II), the tests were run in duplicate, at the dosage levels indicated above, and the mean calculated from the results obtained. It can be seen that the Formula II compound depressed acetate production compared to the negative control, and was comparable to monensin in this regard. This is believed to be an indication that the subject compound is useful as a feed additive in ruminants to enhance feed efficiency, since less energy is wasted in the production of acetate, which, as pointed out above is transformed to methane gas and lost by the animal through eructation. It is expected that a favorable shift to increased propionate production will also become evident by tests to establish optimum dosage level.

Table 2 below summarizes the batch rumen gas production, measuring methane and hydrogen production, and comparing a negative control, a positive control (monensin) and the subject Formula II compound:

TABLE 2

| | Batch Rumen Gas Production | | |
|---|---|---|---|
| Compound | - ppm | $CH_4$ (%) | $H_2$ (%) |
| Control | | 12.1 | 0.0 |
| | | 11.4 | 0.0 |
| | | 11.6 | 0.0 |
| | | 11.7 | 0.0 |
| Average | | 11.7 | 0.0 |
| Formula II | 75 | 11.2 | 0.0 |

TABLE 2-continued

| Compound | Batch Rumen Gas Production | | |
|---|---|---|---|
| | - ppm | CH₄ (%) | H₂ (%) |
| Compound | | 10.8 | 0.0 |
| Average | | 11.0 | 0.0 |
| Percent Change | | −6.0 | |
| Monensin | 12.5 | 5.6 | 0.0 |
| | | 6.2 | 0.0 |
| Average | | 5.8 | 0.0 |
| Percent Change | | −49.4 | |

EXAMPLE 3

The Formula I compound can be complexed with other related metal salts, in addition to copper. These metal salts of Formula I (which include salts of iron and nickel) are then evaluated in the rumen fluid batch culture tests set forth in Example 1, and the results compared to those obtained with the copper complex (Formula II). Test results show that the copper complex gives the best activity.

The subject compounds are closely related to compounds described and claimed in a copending application of the same inventor, assigned to a common assignee and filed on even date herewith, now U.S. Pat. No. 4,421,751 entitled "Bipyridine Substituted Imidazoylidene, Copper Complex, And Its Use In Food-Producing Animals".

I claim:

1. The reaction product of ethylene diamine and 2,2'-dipyridylketone said product being a compound of the formula

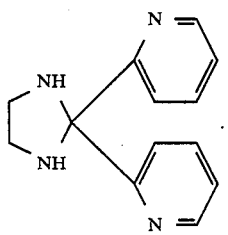

2. A compound selected from the group consisting of

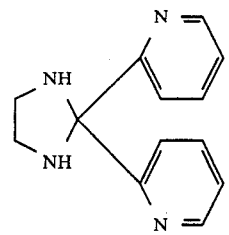

and complexes of that compound with physiologically acceptable cupric, ferrous and nickelous salts.

3. The compound

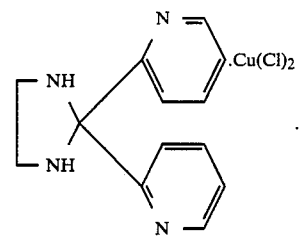

4. A method of enhancing feed efficiency in ruminant animals comprising administering orally to said animals the compound of claim 3 in an amount sufficient to obtain an enhanced feed efficiency response.

5. The method of claim 4, in which the compound is supplied to said ruminant animals in an amount sufficient to maintain about 75 ppm of said compound in the rumen fluid contents of said animals.

6. The compound

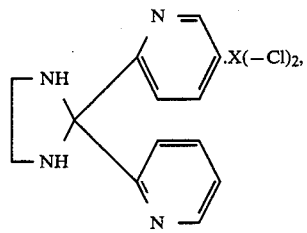

in which X=Cu++, Fe++ and Ni++.

7. An animal feed additive comprising a compound of claim 5, claim 6, claim 2 or claim 1 in an amount effective to enhance feed efficiency.

* * * * *

UNITED STATES PATENT AND TRADEMARK OFFICE
CERTIFICATE OF CORRECTION

PATENT NO. : 4,567,173
DATED : January 28, 1986
INVENTOR(S) : Kurt G. R. Sundelin It is certified that error appears in the above-identified patent and that said Letters Patent are hereby corrected as shown below:

Column 1, line 64, "fercupric" should read --ferrous--.

Column 3, following the formulas, insert --$CuCl_2$ hydrate was dried at 100°C in vacuo--.

Signed and Sealed this

Twentieth Day of May 1986

[SEAL]

Attest:

DONALD J. QUIGG

Attesting Officer

Commissioner of Patents and Trademarks